United States Patent [19]

Smith et al.

[11] Patent Number: 5,245,859
[45] Date of Patent: Sep. 21, 1993

[54] METHOD OF MEASURING CAPILLARY PRESSURES

[75] Inventors: Sidney R. Smith, Lakewood; Richard L. Christiansen, Littleton, both of Colo.

[73] Assignee: Marathon Oil Company, Findlay, Ohio

[21] Appl. No.: 842,820

[22] Filed: Feb. 27, 1992

[51] Int. Cl.⁵ .......................................... G01N 15/08
[52] U.S. Cl. .......................................................... 73/38
[58] Field of Search .............................................. 73/38

[56] References Cited

U.S. PATENT DOCUMENTS

| | | | |
|---|---|---|---|
| 2,724,963 | 11/1955 | Ten Brink | 73/38 |
| 2,737,804 | 3/1956 | Herzog et al. | 73/38 |
| 3,023,606 | 3/1962 | Sarem | 73/38 |
| 3,420,093 | 1/1969 | Collins | 73/38 |
| 4,304,122 | 12/1981 | Tentor | 73/38 |
| 4,625,544 | 12/1986 | Yuan et al. | 73/38 |
| 4,672,840 | 6/1987 | Cullick | 73/38 |
| 4,773,254 | 9/1988 | Shen | 73/38 |
| 5,133,207 | 7/1992 | Wilson et al. | 73/38 |

Primary Examiner—Hezron E. Williams
Assistant Examiner—Joseph W. Roskos
Attorney, Agent, or Firm—Jack L. Hummel; Jack E. Ebel

[57] ABSTRACT

A method for rapidly and accurately determining the threshold and critical capillary pressures of a porous rock sample. A fluid saturating the sample, preferably oil, is withdrawn from the downstream end of the sample at an extremely low rate as a result of the introduction of another fluid, preferably gas, at the upstream end. The other fluid displaces the saturating fluid due to a differential pressure between the upstream and downstream ends of the sample. The differential pressure is created by means which does not require use of back pressure valves, thereby avoiding pressure surges and allowing constant slow withdrawal of the saturating fluid. The threshold and critical capillary pressures may be determined from a trace of the differential pressure.

15 Claims, 2 Drawing Sheets

METHOD OF MEASURING CAPILLARY PRESSURES

FIELD OF THE INVENTION

This invention relates to a method of determining the threshold and critical capillary pressures of liquid saturated porous material. More particularly, it relates to a rapid method of measurement useful in determining threshold and critical capillary pressures of a core sample from a subterranean petroleum reservoir formation.

BACKGROUND OF THE INVENTION

Efficient oil field production requires the recoverable reserves of a reservoir to be estimated periodically. Current practice in reservoir engineering relies heavily on measurement of saturation-dependent relationships of relative permeabilities and capillary pressures. Relative permeabilities combined with absolute permeability reflect flow capacity for a fluid phase for a given pressure drop, while capillary pressure refers to the difference in pressures between two fluids at equilibrium saturations.

Various techniques have been available prior to the present invention for measuring the capillary properties of small core samples. One is the centrifuge technique by which the denser of two phases is drained from a core sample by centrifuging the sample until no further fluid is collected, and repeating this procedure for successively higher accelerations. The capillary pressure and average saturation at each point are computed from the density difference of the fluids, the dimensions of the core and centrifuge, the amount of fluid displaced and the speed of rotation. This procedure provides substantial data about the capillary properties of the sample, but it is quite time consuming, requiring weeks to complete the experiments.

The "restored-state" method of measuring capillary pressure utilizes a porous disc saturated with the wetting fluid which remains impermeable to the non-wetting fluid at the pressures encountered during the test. Wetting fluid is then displaced from the core through the disc by maintaining a constant pressure in the non-wetting phase at the inlet face of the core. A constant pressure is maintained at the outlet face of the disc at a value less than at the inlet. The core is brought to capillary equilibrium when the flow rate ceases and the pressure and saturation distributions of the core sample become uniform. The saturation of the sample is then measured and the difference in pressure between the two phases is the capillary pressure at that saturation. This procedure is repeated at higher inlet pressures, with each stage giving an additional point on the capillary pressure curve, until the desired amount of data is obtained. While this test procedure provides valuable data, it is also time consuming.

While the lengthy procedures of these tests can be justified in order to measure the entire capillary pressure relationship of a sample, it would be desirable to be able to employ a much faster test procedure for the purpose of obtaining information which would allow interpretation of gravity drainage experiments in short core samples, which are typical of cored reservoir rock available for laboratory studies. For this purpose a determination of the threshold and critical capillary pressures is very useful, particularly if these points can be determined at low gas saturations. Test procedures for accurately and rapidly determining these values under the conditions required have not been known, however, prior to the present invention.

BRIEF SUMMARY OF THE INVENTION

In accordance with the invention, a porous core sample saturated with a first fluid is arranged in a holder and a fluid connection is provided between the upstream end of the sample and a second fluid. Although the principle of the invention applies to the determination of threshold and critical capillary pressures of porous material in connection with various combinations of fluids, the gas-oil capillary pressure of reservoir rock samples is of most interest in the application of the invention.

A fluid connection is provided between the downstream end of the sample and a reservoir of the first fluid and the pressure of the first fluid is equilibrated with the pressure in the second fluid. A pressure differential is created between the upstream and downstream ends of the sample so as to cause constant movement of the second fluid into the sample through the upstream end thereof and to displace the first fluid in the sample. The pressure differential is such that the first fluid is displaced at a sufficiently low rate to enable movement of the interface between the first and second fluids to be monitored. The first fluid is thereby withdrawn from the sample while monitoring the movement of the interface, thus enabling the threshold and critical capillary pressures of the samples to be determined.

In order to be able to determine the points of threshold and critical capillary pressures the sample saturating fluid should be withdrawn at a low constant rate. It has been found that this rate should be in the range of 1–100 microliters per hour. The invention is not limited to any one type of withdrawal means but should in any case not require the use of back pressure control valves, as these result in frequent pressure surges which would inhibit the accurate recording of pressure drops that occur when these points are reached. One method which has been found to be of special utility is to pump the second fluid into the upstream end of the sample by a syringe pump, which does not require the use of back pressure valves. Another method is to provide the second fluid in a vessel having a fluid connection to the sample, and to withdraw the saturating fluid from the sample by means of an ultralow rate pump without use of back pressure valves.

As indicated above, the differential pressure of the fluids is monitored to determine the points at which the pressure drops indicating threshold and critical capillary pressures occur. A preferred way to accomplish the monitoring is to produce a trace of the differential pressures against time and to determine the threshold and critical capillary pressures from the trace.

These and other features and aspects of the invention, as well as other benefits, will readily be ascertained from the detailed description of the preferred embodiments described below.

DETAILED DESCRIPTION OF THE PREFERRED EMBODIMENTS

Figure 1:
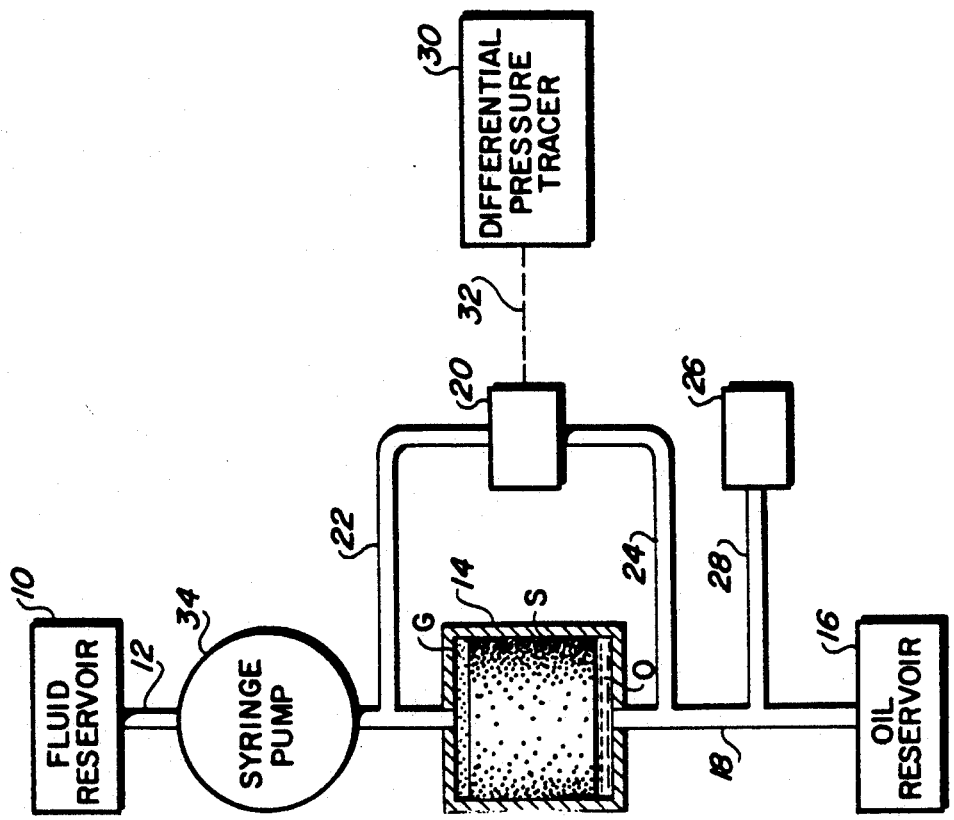
FIG. 1 is a schematic representation, shown partially in section, of the test apparatus used in carrying out a first embodiment of the invention.

Referring to FIG. 1, a first reservoir 10 is connected by conduit 12 to the inlet or upstream end of a core holder 14 and a second reservoir 16 is connected by conduit 18 to the outlet or downstream end of the core holder. A differential pressure transducer 20 is connected by fluid lines 22 and 24 to the conduits 12 and 18, respectively, and an absolute pressure transducer 26 is connected by fluid line 28 to the conduit 18. Differential pressure transcribing means 30 is connected to the differential pressure transducer 20 by a suitable circuit, as indicated by dotted line 32, in order to produce a trace of the differential pressure during the duration of a test. A syringe pump 34 is connected to conduit 12 between the reservoir 10 and the core holder 14 so as to be able to withdraw fluid from the reservoir 10 and inject it into the core.

In conducting a test for determining threshold and critical capillary pressures of a particular fluid-sample system, a porous core sample S is mounted in the core holder 14. Although not shown in detail, the core holder may be of any suitable type having radial overburden capabilities, such as a Hassler core holder. The core sample preferably is flooded with 2–10 pore volumes of the fluid from reservoir 16, with some back pressure, to eliminate free gas saturation in the sample, and, using well known techniques, the pressure in the reservoir 10 is equilibrated with the pressure in the fluid downstream from the sample. With pressures equilibrated, the fluid in the reservoir 10 is pumped into the core sample at a low fixed rate.

Although in the broadest aspect of the invention the test may be conducted with any fluid system the capillary effects of which are desired to be determined, a fluid system commonly of interest in the petroleum industry consists of gas in the reservoir 10 and oil in the reservoir 16. The sample in such a case is a core sample from the reservoir formation of interest which will have been saturated with oil. In such a test arrangement, prior to withdrawing the oil the difference between the pressure measured in the gas phase G at the upstream end of the sample and the pressure measured in the oil phase O at the downstream end of the sample is zero. Gas cannot enter the porous network in the rock sample until the pressure in the gas phase is increased to the point where the gas-oil interface becomes sufficiently deformed so as to penetrate the largest pore throats. At this point the pressure in the gas phase exceeds the pressure in the oil phase by an amount which is the threshold pressure. As pressure in the gas phase is very gradually increased by action of the pump 34, dimples in the gas-oil interface can penetrate the largest pore throats in the rock sample, displacing oil as they advance. As gas pressure continues to build through continued operation of the pump, a connected path will develop through the porous network which allows gas to penetrate from the inlet to the outlet of the sample. When this occurs the gas saturation is known as the critical gas saturation, and the capillary pressure at this point is the critical capillary pressure.

Figure 2A:
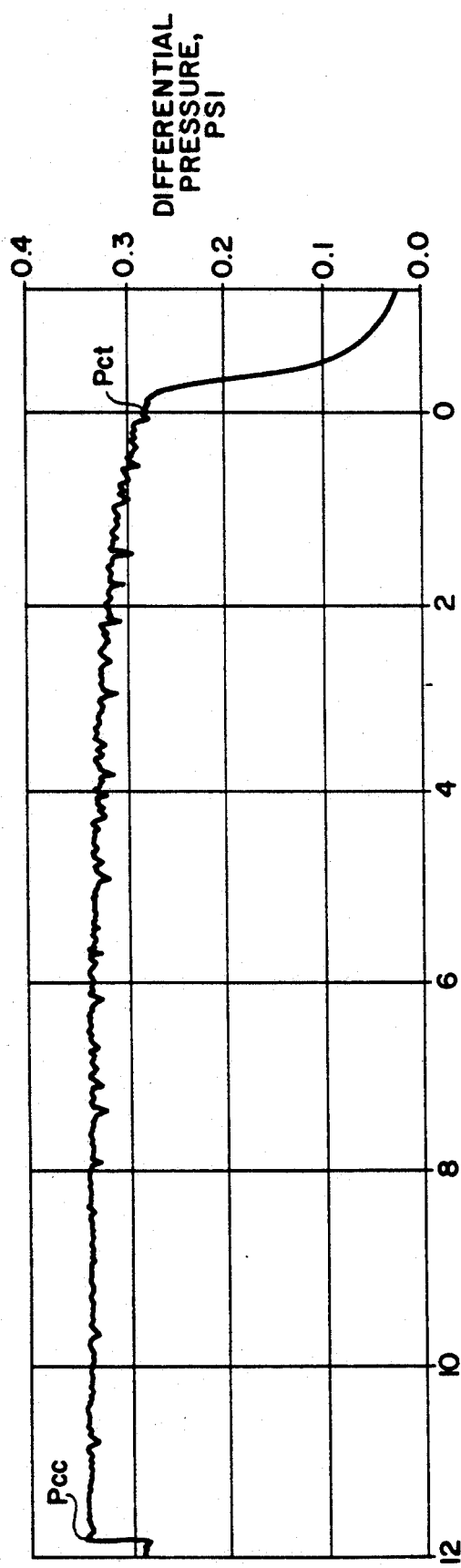
FIG. 2A is a pressure trace produced by the method of the invention from which the threshold and critical capillary pressures of a core sample are determined.

A preferred method of determining the threshold and critical capillary pressures of a particular fluid-rock sample system is illustrated in FIG. 2A, which is a trace of the differential pressure for a core plug measuring one inch in height and one inch in diameter into which gas was pumped at the rate of 0.034 ml per hour. The absence of back pressure valves in the system precluded pressure surges and assured a constant low rate of withdrawal. As shown in the trace, the differential pressure increased, first gradually then at a greater rate, until gas abruptly penetrated through pore throats at the inlet face of the core, which is indicated by the first small drop in pressure. It can be seen that this point, which corresponds to the threshold pressure, occurred at a differential pressure of 0.29 psi, indicated on th trace at the point labeled $P_{ct}$. As the experiment continued a number of additional small pressure drops occurred as gas penetrated through pore throats during its advance from the inlet to the outlet of the core sample. Some of the abrupt pressure drops may correspond to entry of the gas into individual pores but most are likely to have occurred due to entry into a small network of pores.

At gas breakthrough the differential pressure across the core quickly falls to a noticeably lower level. This point, which occurred at 0.34 psi and is indicated on the trace at the point labeled $P_{cc}$, corresponds to the critical capillary pressure of the sample. This result may be further altered for even more precise determination of the critical capillary pressure in order to take into account the gravitational pull of the earth acting on the density difference between the gas and the oil. For the gas and oil employed in the above example, this value was 0.03 psi for a core sample one inch in height. This amount could therefore be subtracted from the observed capillary pressure at gas breakthrough. Alternatively, shorter core samples can be employed to minimize the effects of gravity.

During the experiment depicted in FIG. 2A, 11.8 hours elapsed from the point at which gas entered the porous network of the sample until gas breakthrough. At a constant withdrawal of oil at the rate of 0.034 ml per hour, the total amount of oil withdrawn was 0.401 ml. The ratio of this amount to the pore volume of the sample yields the critical gas saturation, which as stated previously is the gas saturation required to establish a connected path for flow of gas through the core sample. In the case of the example, the total pore volume of the sample was 2.63 ml, resulting in a critical gas saturation of 15.2%.

The determinations of threshold and critical capillary pressures by the means of the invention have been shown by qualitative error analysis to be accurate to 0.05 psi. This level of accuracy would be very difficult to obtain in a centrifuge test approach.

The importance of avoiding pressure surges and maintaining a constant withdrawal rate can now be better appreciated. If a pressure drop or increase appears on the trace but is unrelated to pressure behavior caused by penetration of gas into pore throats or gas breakthrough, the significance of the phenomenon could easily be misinterpreted, resulting in the threshold and critical capillary pressures erroneously being determined. Similarly, if the rate of withdrawal were to suddenly increase or decrease, the trace would no longer be an accurate means of determining these capillary pressure points.

Figure 2B:
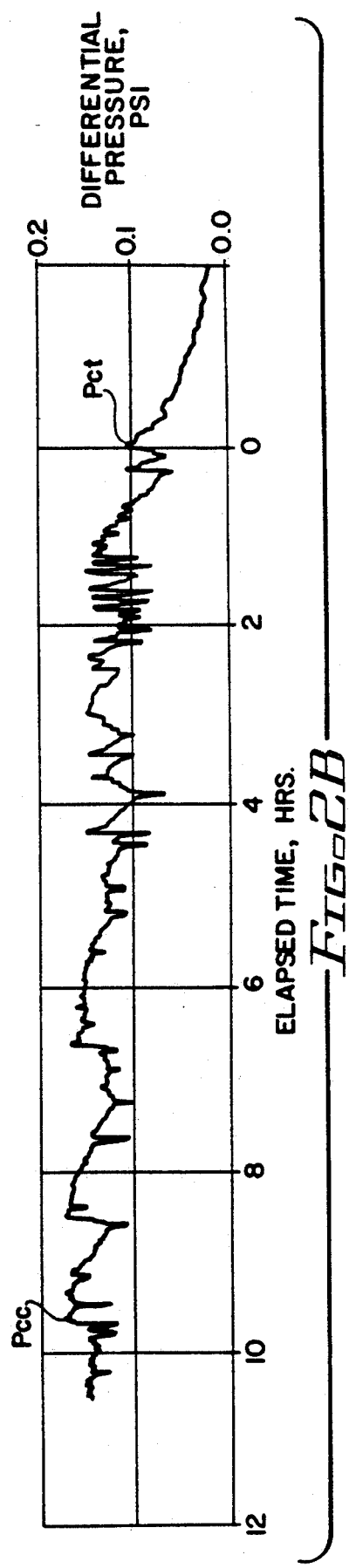
FIG. 2B is another pressure trace produced for a different core sample.

Another example of the method is illustrated in FIG. 2B, which shows the trace of a test run with a different core plug. The threshold capillary pressure of 0.10 psi at point $P_{ct}$ is relatively simple to identify. The jagged and irregular features of the trace represent alternating penetration of gas through the tight matrix and molds of the sample, which has a different structure from the sample of FIG. 2A. The large sawtooth features starting at about 1.2 hours and 3.2 hours very likely result from sequential incidents of snap-off of gas bubbles entering molds, which make the trace subject to individual interpretation more so than the trace of FIG. 2A. The point at which gas breakthrough occurred can be seen to be 0.18 psi and has been labeled $P_{cc}$ on the trace. The total amount of oil withdrawn during the experiment at 0.034 ml per hour was 0.330 ml, which when divided by the sample pore volume of 3.10 ml yields a critical gas saturation of 10.6%.

Since a syringe pump can inject gas into the core holder at a constant low rate without requiring back pressure control valves to regulate the pressure, the surges associated with back pressure control regulators are avoided. A syringe pump can be expected to operate within the context of the present invention at a rate in the range of 1-100 microliters per hour. Although any syringe pump capable of injecting fluid at a sufficiently low constant rate may employed, an example of a syringe pump suitable for use in the invention is Harvard Microliter Syringe Pump 2274.

Figure 3:
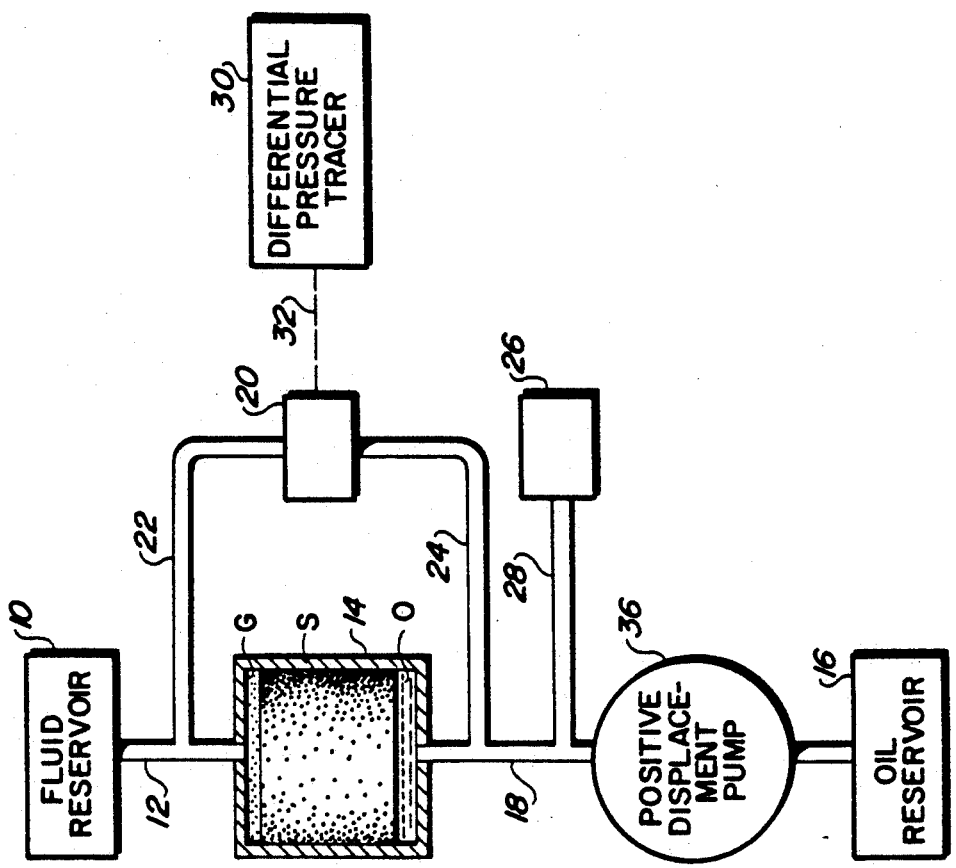
FIG. 3 is a schematic representation similar to that of FIG. 1, but showing test apparatus for carrying out another embodiment of the invention.

A different way of creating a pressure drop across a core sample is illustrated in FIG. 3, wherein the syringe pump 34 of FIG. 1 is removed from the system and a positive displacement pump 36 is connected to conduit 18 between the oil reservoir 16 and the fluid line 28 so as to be able to pump fluid from the core holder into the reservoir 16. Any positive displacement pump capable of operating at a sufficiently low rate to enable accurate monitoring of the test may be used. An example of such a pump is available from Ruska Corporation. Pump rates in the range of 0.012-0.10 ml per hour when employing a positive displacement pump are contemplated. The pump rate should not be so low, however, that the negative effects of movement of pressure seals in the pump and thermal expansion of fluids outweigh desired flow rates. At low flow rates it is helpful to frequently calibrate the differential pressure transducer to ensure accurate measurement of pressure drop. It will be understood that withdrawal of oil from the sample results in a pressure drop across the sample, causing fluid from the reservoir 10 to flow toward and penetrate the sample.

Whether liquid is withdrawn from a core sample by means of a positive displacement pump or due to injection of fluid into the inlet face of the sample, the rate of withdrawal should be maintained in the range of 1-100 microliters per hour in order to produce a slow enough rate to permit accurate pressure monitoring.

As previously mentioned, although the invention has been described mainly in the context of studies involving porous oil-bearing rock formations in which gas is the fluid used to drive oil from the pores, the invention may also be carried out using other fluids, such as brine, oil or a brine and surfactant solution.

It will now be appreciated that the invention enables the threshold and critical capillary pressures of a fluid-sample system to be accurately determined in a relatively short period of time with simple test apparatus. It will also be understood that changes to other features and aspects which do not affect the overall basic function and concept of the invention may be made by those skilled in the art without departing from the spirit and scope of the invention, as defined by the appended claims.

What is claimed is:

1. A method of measuring threshold and critical capillary pressures of a porous core sample saturated with a first fluid, comprising:
   arranging the core sample in a holder so as to have an upstream end and a downstream end;
   providing a fluid connection between the upstream end of the sample and a second fluid;
   providing a fluid connection between the downstream end of the sample and a reservoir of the first fluid;
   equilibrating the pressure of the first fluid with the pressure in the second fluid;
   creating a pressure differential between the upstream and downstream ends of the sample so as to cause constant movement of the second fluid into the sample through the upstream end thereof and to displace the first fluid in the sample;
   the pressure differential being such as to cause displacement of the first fluid at a sufficiently low rate to enable movement of the interface between the first and second fluids to be monitored; and
   withdrawing the first fluid from the sample while monitoring the movement of said interface to determine the threshold and critical capillary pressures of the sample.

2. The method of claim 1, wherein the first fluid is withdrawn from the sample at a rate in the range of 1-100 microliters per hour.

3. The method of claim 1, wherein the second fluid is a gas contained in a vessel, the pressure differential between the upstream and downstream ends of the sample being created by withdrawing the first fluid from the sample by means of a pump without use of back pressure valves.

4. The method of claim 3, wherein the pump is a positive displacement pump.

5. The method of claim 4, wherein the first fluid is withdrawn from the sample at a rate in the range of 1-100 microliters per hour.

6. The method of claim 1, wherein the second fluid is gas pumped into the upstream end of the sample by a syringe pump, without the use of back pressure valves.

7. The method of claim 6, wherein the first fluid is withdrawn from the sample at a rate in the range of 1-100 microliters per hour.

8. The method of claim 1, wherein the first fluid is oil and the second fluid is gas.

9. The method of claim 1, wherein the movement of the interface between the first and second fluids is monitored by measuring the differential pressure between the upstream and downstream ends of the sample.

10. The method of claim 9, wherein the threshold capillary pressure is determined by a first relatively small drop in the differential pressure and wherein the critical capillary pressure is determined by an abrupt relatively large drop in the differential pressure.

11. The method of claim 10, including the step of producing a trace of the differential pressure and determining the threshold and critical capillary pressures from the trace.

12. A method of measuring threshold and critical capillary pressures of a porous rock core sample saturated with oil, comprising:

arranging the core sample in a holder so as to have an upstream end and a downstream end;

providing a fluid connection between the upstream end of the sample and a source of gas;

providing a fluid connection between the downstream end of the sample and a reservoir of oil;

equilibrating the pressure of the gas with the pressure in the oil;

creating a pressure differential between the upstream and downstream ends of the sample so as to cause constant movement of the gas into the sample through the upstream end thereof and to displace oil from the sample;

the pressure differential being such as to cause displacement of the oil at a rate in the range of 1-100 microliters per hour; and withdrawing the oil from the sample while monitoring the movement of said interface to determine the threshold and critical capillary pressures of the sample.

13. The method of claim 12, wherein the gas is contained in a vessel, the pressure differential between the upstream and downstream ends of the sample being created by withdrawing the oil from the sample by means of a positive displacement pump without use of back pressure valves.

14. The method of claim 12, wherein the pressure differential is created by pumping the gas into the upstream end of the sample by a syringe pump, without the use of back pressure valves.

15. The method of claim 12, wherein the movement of the interface between the gas and oil is monitored by measuring the differential pressure between the upstream and downstream ends of the sample and creating a trace thereof, the threshold capillary pressure being indicated on the trace by a first relatively small drop in the differential pressure and the critical capillary pressure being indicated on the trace by an abrupt relatively large drop in the differential pressure.

* * * * *